United States Patent
Salkic

(10) Patent No.: US 12,329,873 B2
(45) Date of Patent: Jun. 17, 2025

(54) DOOR HANDLE DEVICE FOR A VEHICLE DOOR

(71) Applicant: MERCEDES-BENZ GROUP AG, Stuttgart (DE)

(72) Inventor: Asmir Salkic, Ulm (DE)

(73) Assignee: MERCEDES-BENZ GROUP AG, Stuttgart (DE)

( * ) Notice: Subject to any disclaimer, the term of this patent is extended or adjusted under 35 U.S.C. 154(b) by 94 days.

(21) Appl. No.: 18/286,570

(22) PCT Filed: Mar. 31, 2022

(86) PCT No.: PCT/EP2022/058562
§ 371 (c)(1),
(2) Date: Oct. 12, 2023

(87) PCT Pub. No.: WO2022/218718
PCT Pub. Date: Oct. 20, 2022

(65) Prior Publication Data
US 2024/0189473 A1 Jun. 13, 2024

(30) Foreign Application Priority Data
Apr. 13, 2021 (DE) ............ 10 2021 001 929.6

(51) Int. Cl.
*A61L 2/26* (2006.01)
*A61L 2/10* (2006.01)
(Continued)

(52) U.S. Cl.
CPC ............ *A61L 2/26* (2013.01); *A61L 2/10* (2013.01); *A61L 2/202* (2013.01); *E05B 85/107* (2013.01); *A61L 2202/11* (2013.01)

(58) Field of Classification Search
CPC .......... E05B 1/0069; E05B 85/10; A61L 2/10; A61L 2/26; A61L 2/202
See application file for complete search history.

(56) References Cited

U.S. PATENT DOCUMENTS

2020/0095799 A1 3/2020 Gerardiere et al.
2021/0316026 A1* 10/2021 Ruse .................. B62D 1/04
(Continued)

FOREIGN PATENT DOCUMENTS

| CA | 3100907 A1 | 12/2019 |
| CN | 108104622 A | 6/2018 |

(Continued)

OTHER PUBLICATIONS

DE 102015014223 Translation (Year: 2016).*
(Continued)

*Primary Examiner* — Christine M Mills
*Assistant Examiner* — Yahya Sidky
(74) *Attorney, Agent, or Firm* — PATENT PORTFOLIO BUILDERS PLLC

(57) ABSTRACT

A door handle device for a vehicle door of a motor vehicle includes a handle part and a cleaning device emitting UV-C light. The handle part is adjustable at least between a retracted non-use position and an extended use position. The cleaning device is configured in such a way that it loads the handle part in its non-use position with UV-C light and cleans it as a result.

16 Claims, 1 Drawing Sheet

Figure 1:
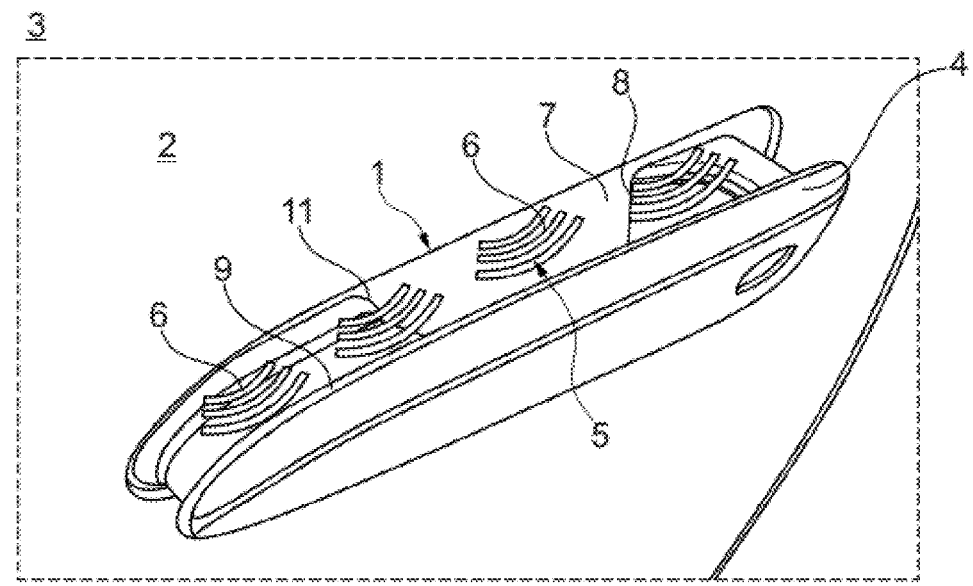

(51) Int. Cl.
*A61L 2/20* (2006.01)
*E05B 85/10* (2014.01)

(56) References Cited

U.S. PATENT DOCUMENTS

2021/0393831 A1* 12/2021 Harris .................... E05B 85/16
2023/0304318 A1    9/2023 Park et al.

FOREIGN PATENT DOCUMENTS

| DE | 102012006972 A1 | 10/2013 |
| DE | 102015014223 A1 | 5/2016 |
| JP | 2009111208 A | 5/2009 |
| JP | 2020022715 A | 2/2020 |
| KR | 101331796 B1 | 11/2013 |
| WO | 2019237001 A1 | 12/2019 |
| WO | 2022045496 A1 | 3/2022 |

OTHER PUBLICATIONS

JP 2009111208 Translation (Year: 2009).*
International Search Report and Written Opinion mailed Aug. 10, 2022 in related/corresponding International Application No. PCT/EP2022/058562.
Office Action created Jan. 12, 2022 in related/corresponding DE Application No. 10 2021 001 929.6.
Office Action dated Oct. 23, 2024 in related/corresponding KR Application No. 10-2023-7034584.
Office Action dated Jul. 29, 2024 in related/corresponding JP Application No. 2023-560852.

* cited by examiner

DOOR HANDLE DEVICE FOR A VEHICLE DOOR

BACKGROUND AND SUMMARY OF THE INVENTION

Exemplary embodiments of the present invention relate to a door handle device for a vehicle door of a motor vehicle, a motor vehicle with a vehicle door and such a door handle device, and a method for cleaning a handle part of such a door handle device.

In order to be able to meet the highest design and aerodynamic standards in modern motor vehicles, lowerable door handles are often offered, these being arranged to be lowered and therefore invisible when not in use. Only when a user approaches does the handle part extend to its use position and thereby enable the vehicle door to be opened.

However, in the case of door handle devices with lowerable handle parts, the door handle device or at least the handle part is difficult to clean and it is impossible to do so in its non-use position. In car washes, in which motor vehicles are usually closed, the handle part is also in its retracted non-use position and is therefore not cleaned there either. Furthermore, if the motor vehicle is used by different users, it would also be of great benefit to be able to clean the handle part or even disinfect it in order, in particular, to prevent the transmission of infectious diseases.

CN 108104622 A discloses a generic door handle device for a vehicle door of a motor vehicle with a handle part and a cleaning device emitting UV-C light. In the known door handle device, the handle part or a handle recess are loaded with UV-C light for disinfection. The incidence of the UV-C light on oxygen in the air also produces ozone, so the disinfecting effect can be further increased.

Exemplary embodiments of the present invention address the problem of providing, for a door handle device of the generic type, an improved or at least an alternative embodiment which is distinguished, in particular, by greater hygiene and improved optics and a better design.

The present invention is based on the general idea of equipping a door handle device with a lowerable handle part and, if it is retracted into a handle recess, that is to say an interior space, of loading this handle part with UV-C light and thereby disinfecting it. The door handle device for a vehicle door of a motor vehicle according to the invention possesses the abovementioned handle part and a cleaning device which is configured to emit UV-C light here. Such UV-C light usually has a wavelength <265 nm. According to the invention, the handle part can now be adjusted at least between a retracted non-use position and an extended use position, the cleaning device being configured such that it loads the handle part in its non-use position with UV-C light and cleans it as a result. The door handle device according to the invention therefore offers for the first time, with respect to a lowerable handle part, the possibility of the latter being cleaned when in its retracted state and therefore of hygiene being increased overall. Because it is possible to retract the handle part, aerodynamic, design and optical advantages can also be achieved. In its non-use position, the handle part is retracted into an interior space of the motor vehicle door here and can be loaded with UV-C light there, preferably when in its closed state. The UV-C light is able to kill bacteria, viruses, and germs here, the oxygen present in the interior space at the same time being converted into ozone through incidence of the UV-C light and therefore likewise contributing to the disinfection and the improved hygiene. UV-C light is a virucide here, so it can disable or kill viruses. With the door handle device according to the invention, a lowerable handle part that is able to meet the highest aerodynamic and design standards, can therefore be disinfected in its non-use state, thereby enabling the transmission of diseases to be avoided or the risk of such transmission to at least be reduced, in particular when the vehicle is being used by different people.

Preferably, according to a refinement of the invention, provision is made for the cleaning device to have a plurality of light sources that emit the UV-C light and that provide all-round lighting or lighting of the main sections of the handle part. The main sections of the handle part are the sections that a person touches when operating the handle part. In a preferred embodiment, provision is made for the light sources to be arranged in a circle around the handle part and spaced apart from one another, this allowing the all-round lighting of the handle part and/or the main sections thereof which may also be referred to as the contact surfaces. The light sources are arranged on the vehicle door, in particular on a handle recess, in which the handle part rests in its non-use position.

In an advantageous refinement of the solution according to the invention, provision is made for a door handle housing into which the handle part is at least partially retracted in its non-use position. In its retracted non-use position, the handle part is tightly connected to the door handle housing here and tightly encloses from the outside an interior space in which the handle part is arranged. This makes it possible for the handle part to be arranged in a protected space that is closed off from the outside environment in its non-use position and to be disinfected there at the same time. In its non-use state, the handle part is therefore protected from external dirt and can be disinfected and is also protected from external environmental influences in this non-use position.

In a further advantageous embodiment of the door handle device according to the invention, provision is made for a container of oxygen via which oxygen can be output into the interior space in which the handle part is located in the non-use position. It is thereby possible, in addition to the UV-C light which on its own already has a virucidal effect, to generate ozone through addition of oxygen and UV-C light which likewise kills bacteria and viruses and germs and also has a fungicidal effect. A particularly hygienic handle part can also be achieved hereby, thus making it possible to at least reduce the risk of diseases being transmitted on this handle part.

In an advantageous refinement of the solution according to the invention, provision is made for a backflow space connected to the interior space on the input side and to the container on the output side, via which oxygen or ozone flows back from the interior space via the backflow space into the container. Through at least one such backflow space, a closed system can be produced between the container, the interior space, and the at least one backflow space, thus minimizing any loss of oxygen and thereby allowing a particularly long useful life. It is also of great advantage that, as a result of such a closed system, virtually no ozone reaches the outside, it instead being retained in the circuit and being usable again and again to disinfect the handle part. Owing to the fact that the disinfection of the handle part, for example the loading with UV-C light or with oxygen, takes place only, that is to say exclusively, when the handle part has been retracted into the door housing, that is to say with the handle part lowered, an extremely economical consumption of oxygen can also be achieved.

In an advantageous refinement of the door handle device according to the invention, a check valve allowing flow in the direction of the interior space is arranged between the container and the interior space. A check valve allowing flow in the direction of the backflow space may also be arranged between the interior space and the backflow space, it indeed also being possible to arrange between the backflow space and the container a check valve allowing flow in the direction of the container. This allows a circulating circuit of oxygen or ozone, going from the container via the interior space and from the latter via the at least one backflow space back into the container, without having to fear any uncontrolled backflows here. Such check valves may be configured comparatively simply and inexpensively, for example as flap valves or as spring-loaded valves, which only open when a predefined pressure difference has been reached.

In a further advantageous embodiment, provision is made for a pump via which oxygen can be pumped out of the container into the interior space. This pump provides for an excess pressure in the container, as a result of which the check valve or excess pressure valve located between the container and the interior space opens and allows oxygen to emerge into the interior space. Through the loading of the oxygen with UV-C light, the latter is converted into ozone in the interior space and the handle part is thereby disinfected. As a result of the pumping of oxygen into the interior space, the pressure in the interior space also rises, this pressure being unable to escape outside due to the seal between the handle part and the door housing so that, from a predefined excess pressure in the interior space, the check valve arranged between the interior space and the backflow space opens and oxygen or ozone passes from the interior space into the backflow space. The oxygen or the ozone may be fed back to the container via the latter.

Generally speaking, UV-C light has a wavelength between 100 nm<<280 nm, it having been shown in experiments that, in particular, a wavelength of <242 nm acts particularly effectively against bacteria, germs, or viruses, but also odor molecules.

The present invention is further based on the general idea of equipping a motor vehicle with a vehicle door and a door handle device described in the previous paragraphs and thereby transferring the advantages described in relation to the door handle device according to the invention to the motor vehicle. Specifically, this is, in particular, a simple and inexpensive disinfecting of the handle part and therefore an improvement in hygiene, with at the same time durable operability through, for example, a closed oxygen-ozone circuit and a very attractive door handle design thanks to the lowerable handle part.

The present invention is further based on the general idea of providing a method for cleaning a handle part of a door handle device on a motor vehicle in which the handle part is first of all transferred into its retracted non-use position. Then, the cleaning device loads the interior space with UV-C light, at the same time oxygen being emitted from the container into the interior space and converted into ozone there as a result of the UV-C light and disinfects the handle part as a result. The advantage of the method according to the invention lies, in particular, in reliably removing viruses, bacteria, spores, germs, but also odor molecules, from the handle part in its non-use position and thereby allowing particularly hygienic handling. Particularly in times of highly infectious diseases, this constitutes a considerable advantage.

In the method according to the invention, a backflow space may of course also be provided alongside an interior space so that, via a corresponding pump, oxygen or, if applicable, also ozone may periodically or permanently be pumped out of a container into the interior space in which the handle part is located in its retracted non-use position, and flows back into the container via the backflow space. It is thereby possible to achieve a temporary disinfecting of the handle part exclusively with its handle part located in its non-use position so as to allow inexpensive operation.

Further important features and advantages of the invention are set out in the sub-claims, in the drawings and in the associated description of the figures by reference to the drawings.

It is self-evident that the features mentioned above and those yet to be explained below can be used not only in the combination specified, but also in other combinations or on their own without leaving the scope of the present invention.

Preferred exemplary embodiments of the invention are shown in the drawings and are explained in more detail in the following description, identical reference numerals relating to the same or similar or functionally the same components.

BRIEF DESCRIPTION OF THE DRAWING FIGURES

Figure 2:
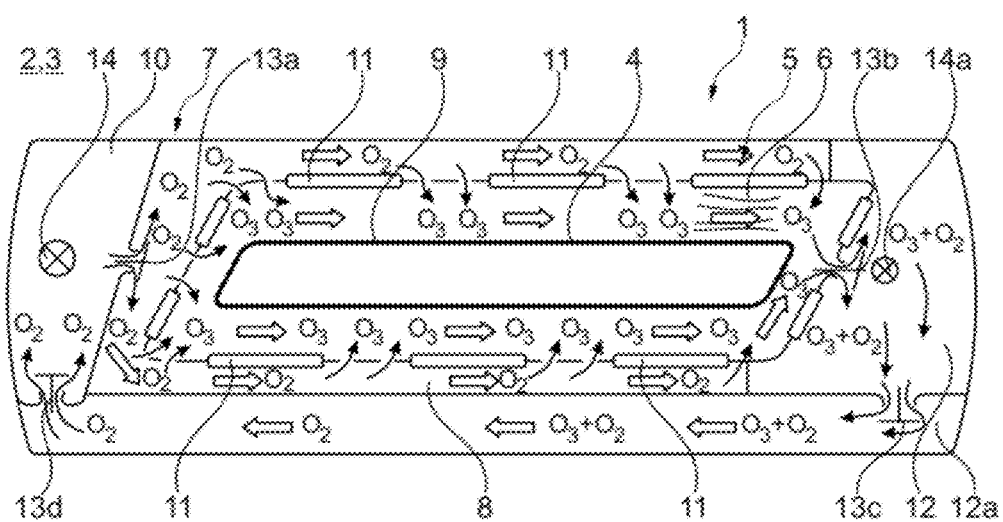

The following figures show, in each case schematically:

FIG. 1 An external view of a motor vehicle according to the invention with a door handle device according to the invention;

FIG. 2 A sectional representation through the door handle device according to the invention in a specific embodiment.

DETAILED DESCRIPTION

According to FIG. 1, a door handle device 1 for a vehicle door 2 of a motor vehicle 3 according to the invention has a handle part 4, which can be adjusted between a non-use position retracted in the vehicle door 2 (cf. FIG. 2) and an extended use position (cf. FIG. 1). According to the invention, provision is now made for a cleaning device 5 that emits UV-C light 6 and is arranged in a handle recess (not shown in any greater detail) provided in the vehicle door and is configured such that it loads the handle part 4 or a part of the handle part 4 lying inside in its non-use position with UV-C light 6 and cleans it as a result. UV-C light 6 has an antibacterial, fungicidal and virucidal effect here and also kills germs and neutralizes odors. Departing from the situation shown according to FIG. 1, the cleaning device 5 emits UV-C light 6 only if the handle part 4 is in its retracted non-use position in which it preferably closes flush with the surface of the vehicle door 2. Alternatively, it may also be entirely lowered in the vehicle door 2.

The door handle device 1 according to the invention also has a door handle housing 7 (cf. FIG. 2) into which the handle part 4 is at least partially retracted in its non-use position. In its non-use position, the handle part 4 closes tightly with the door handle housing 7 and thereby delimits an interior space 8 in which the handle part 4 is arranged and also seals the latter from the outside. In addition, an outer seal 9 may be arranged on the handle part 4.

In the vehicle door 2, provision may also be made for a container 10 (cf. FIG. 2) of oxygen via which oxygen can be output into the interior space 8. As a result of the outputting of oxygen $O_2$ into the interior space 8 and the simultaneous loading of the oxygen with UV-C light 6, ozone $O_3$ forms, which likewise has an antibacterial, fungicidal and virucidal effects and acts against germs and odor molecules.

The cleaning device 5 may have a plurality of light sources 11 here that emit the UV-C light 6 and provide all-round lighting at least in the interior space 8, that is to say inner-lying parts of the handle part 4 and therefore disinfection of the same. If, as described above, the handle part 4 is entirely lowered in the handle recess, not only could sections of the handle part 4 therefore be lit, but instead the entire handle part 4 could also be lit. As can be seen from FIG. 2, the light sources 11 are arranged, for example, in a circle around the handle part 4 and spaced apart from one another, meaning that both reliable illumination or lighting of the handle part 4 and reliable mixing of the air inside the interior space 8 with oxygen and ozone and therefore an extremely high disinfecting effect can be achieved.

Provision may also be made for a backflow space 12 that is connected either directly or indirectly to the interior space 8 on the input side and to the container 10 on the output side via a further backflow space 12*a* (cf. FIG. 2). Via this backflow space 12 or via the backflow spaces 12, 12*a*, it is possible to guide oxygen or ozone from the interior space 8 back into the container 10 and thereby to enable particularly economical operation of the cleaning device 5.

In order to prevent undesirable backflows of oxygen or ozone, a check valve 13*a* allowing flow in the direction of the interior space 8 may be provided between the container 10 and the interior space 8, it being possible to arrange a check valve 13*b* allowing flow in the direction of the backflow space 12 between the interior space 8 and the backflow space 12. If a further backflow space 12*a* is provided, then a check valve 13*c* may also be provided between the latter and the backflow space 12 and a check valve 13*d* may be provided between the backflow space 12*a* and the container 10. The check valves 13*a*, 13*b*, 13*c* and 13*d* provide a circular flow of the oxygen or of the ozone here and open when a predefined pressure difference is reached.

In order to enable oxygen to be conveyed from the container 2 into the interior space 8, provision may be made for a pump 14 via which oxygen is pumped out of the container 10 into the interior space 8. A further pump 14*a* may also be arranged in the backflow space 12 and ensures that oxygen or ozone is sucked out of the interior space 8 and transported on to the backflow space 12*a* or to the container 10.

Alongside the door handle device 1 according to the invention, protection is also to be sought for a motor vehicle 3 with a vehicle door 2 and such a door handle device 1.

Generally speaking, the handle part 4 of the door handle device 1 described in the previous paragraphs is cleaned as follows here:

First of all, the handle part 4 is transferred into its retracted non-use position, whereupon the cleaning device 5 loads the interior space 8 with UV-C light 6. This UV-C light 6 can be used to carry out disinfection and, in particular, to kill viruses, germs, fungi and bacteria and to neutralize odor molecules. In addition, it is also conceivable for oxygen to be emitted from the container 10 into the interior space 8 and to be converted into ozone there as a result of the UV-C light 6 emitted from the cleaning device 5 and thereby to disinfect the handle part 4.

All in all, the door handle device 1 according to the invention and the motor vehicle 3 according to the invention can be used to produce for the first time a visually attractive, aerodynamically favorable, and at the same time extremely hygienic door handle device 1 which preferably disinfects the handle part 4 every time the handle part 4 is retracted into its non-use position.

Although the invention has been illustrated and described in detail by way of preferred embodiments, the invention is not limited by the examples disclosed, and other variations can be derived from these by the person skilled in the art without leaving the scope of the invention. It is therefore clear that there is a plurality of possible variations. It is also clear that embodiments stated by way of example are only really examples that are not to be seen as limiting the scope, application possibilities or configuration of the invention in any way. In fact, the preceding description and the description of the figures enable the person skilled in the art to implement the exemplary embodiments in concrete manner, wherein, with the knowledge of the disclosed inventive concept, the person skilled in the art is able to undertake various changes, for example, with regard to the functioning or arrangement of individual elements stated in an exemplary embodiment without leaving the scope of the invention, which is defined by the claims and their legal equivalents, such as further explanations in the description.

The invention claimed is:

1. A door handle device for a vehicle door of a motor vehicle, the door handle device comprising:
   a handle part adjustable at least between a retracted non-use position and an extended use position;
   a cleaning device that emits UV-C light and is a component of the handle part, wherein the cleaning device is configured such that the cleaning device loads the handle part in the retracted non-use position with UV-C light and cleans the handle part using the UV-C light;
   a door handle housing into which the handle part is at least partially retracted in the retracted non-use position, wherein in the retracted non-use position, the handle part is tightly connected to the door handle housing and tightly encloses from an outside an interior space in which the handle part is arranged;
   a container of oxygen via which oxygen is suppliable to the interior space; and
   a backflow space connected to the interior space on an input side and to the container on an output side, via which oxygen or ozone flows back from the interior space via the backflow space into the container.

2. The door handle device of claim 1, wherein the cleaning device has a plurality of light sources that emit the UV-C light and that provide all-round lighting of contact surfaces of the handle part or of the entire handle part.

3. The door handle device of claim 2, wherein the plurality of light sources are arranged in a circle around the handle part and are spaced apart from one another.

4. The door handle device of claim 1, further comprising:
   a first check valve configured to allow flow in a direction of the interior space and arranged between the container and the interior space, or
   a second check valve configured to allow flow in a direction of the backflow space and arranged between the interior space and the backflow space.

5. The door handle device of claim 4, further comprising:
   a third check valve configured to allow flow in a direction of the container and arranged between the backflow space and the container.

6. The door handle device of claim 1, wherein
   the door handle device further comprises a pump via which oxygen is pumpable out of the container into the interior space, or
   the cleaning device emits UV-C light with a wavelength <242 nm.

7. A motor vehicle, comprising:
a vehicle door; and
a door handle device as a component of the vehicle door, wherein the door handle device comprises
a handle part adjustable at least between a retracted non-use position and an extended use position;
a cleaning device that emits UV-C light and is a component of the handle part, wherein the cleaning device is configured such that the cleaning device loads the handle part in the retracted non-use position with UV-C light and cleans the handle part using the UV-C light;
a door handle housing into which the handle part is at least partially retracted in the retracted non-use position, wherein in the retracted non-use position, the handle part is tightly connected to the door handle housing and tightly encloses from an outside an interior space in which the handle part is arranged;
a container of oxygen via which oxygen is suppliable to the interior space; and
a backflow space connected to the interior space on an input side and to the container on an output side, via which oxygen or ozone flows back from the interior space via the backflow space into the container.

8. The motor vehicle of claim 7, wherein the cleaning device has a plurality of light sources that emit the UV-C light and that provide all-round lighting of contact surfaces of the handle part or of the entire handle part.

9. The motor vehicle of claim 8, wherein the plurality of light sources are arranged in a circle around the handle part and are spaced apart from one another.

10. The motor vehicle of claim 7, further comprising:
a first check valve configured to allow flow in a direction of the interior space and arranged between the container and the interior space, or
a second check valve configured to allow flow in a direction of the backflow space and arranged between the interior space and the backflow space.

11. The motor vehicle of claim 10, further comprising:
a third check valve configured to allow flow in a direction of the container and arranged between the backflow space and the container.

12. The motor vehicle of claim 7, wherein
the door handle device further comprises a pump via which oxygen is pumpable out of the container into the interior space, or
the cleaning device emits UV-C light with a wavelength <242 nm.

13. A method for cleaning and disinfecting a handle part of a door handle device, which comprises the handle part adjustable at least between a retracted non-use position and an extended use position and a cleaning device that emits UV-C light and is a component of the handle part, wherein the method comprises:
transferring the handle part into the retracted non-use position, wherein in the retracted non-use position the handle part is at least partially retracted into a door handle housing and the handle part is tightly connected to the door handle housing and tightly encloses from an outside an interior space in which the handle part is arranged;
loading, by the cleaning device, the interior space surrounding the handle part in the retracted non-use position with UV-C light; and
emitting oxygen from a container into the interior space and converting the emitted oxygen into ozone as a result of the UV-C light to disinfect the handle part and flowing the oxygen or the ozone back from the interior space into the container via a backflow space connected to the interior space on an input side and to the container on an output side.

14. The method of claim 13, further comprising:
allowing, via a first check valve, flow in a direction of the interior space and arranged between the container and the interior space.

15. The method of claim 14, further comprising:
allowing, via a second check valve, flow in a direction of the backflow space and arranged between the interior space and the backflow space.

16. The method of claim 15, further comprising:
allowing, via a third check valve, flow in a direction of the container and arranged between the backflow space and the container.

* * * * *